United States Patent
Charles, Jr. et al.

(10) Patent No.: US 9,486,139 B2
(45) Date of Patent: Nov. 8, 2016

(54) GARMENT FOR MONITORING PHYSIOLOGICAL FUNCTIONS AND METHOD OF USE THEREOF

(71) Applicant: The Johns Hopkins University, Baltimore, MD (US)

(72) Inventors: Harry K. Charles, Jr., Laurel, MD (US); Russell P. Cain, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 295 days.

(21) Appl. No.: 14/271,484

(22) Filed: May 7, 2014

(65) Prior Publication Data

US 2014/0243618 A1    Aug. 28, 2014

Related U.S. Application Data

(62) Division of application No. 12/503,600, filed on Jul. 15, 2009, now Pat. No. 8,758,241.

(60) Provisional application No. 61/080,704, filed on Jul. 15, 2008.

(51) Int. Cl.
*A61B 5/00* (2006.01)
*G06F 19/00* (2011.01)
(Continued)

(52) U.S. Cl.
CPC ............ *A61B 5/0002* (2013.01); *A41D 1/002* (2013.01); *A61B 5/6804* (2013.01); *A61B 5/72* (2013.01); *G06F 1/163* (2013.01); *G06F 19/325* (2013.01); *G06F 19/3412* (2013.01);
(Continued)

(58) Field of Classification Search
CPC ........ A61B 5/72; A61B 5/0024; A61B 5/68; G06F 1/163; G06F 19/325; G06F 19/3412; A41D 1/002
See application file for complete search history.

(56) References Cited

U.S. PATENT DOCUMENTS 5,321,240 A    6/1994 Takahira
5,480,842 A    1/1996 Clifton et al.
(Continued)

FOREIGN PATENT DOCUMENTS

JP     0670897    3/1994
WO    99/64657   12/1999

OTHER PUBLICATIONS

Axisa, F et al; "Wrist Ambulatory Monitoring System and Smart Glove for Real Time Emotional, Sensorial and Physiological Analysis"; Proceedings of the 26th Annual International Conference of the IEEE EMBS San Francisco, CA, USA, Sep. 1-5, 2004, p. 2161-2164.

(Continued)

*Primary Examiner* — William Thomson
*Assistant Examiner* — Marie Archer
(74) *Attorney, Agent, or Firm* — Noah J. Hayward

(57) ABSTRACT

A plurality of sensors are embedded in a form fitting garment similar to exercise togs such that the sensors are held in contact with or close proximity to the body. The sensors are connected via a plurality wires to an electronics module which is unintrusive being literally in its ultimate configuration the size of a credit card. A range of thickness, from 6 mm (6 credit cards) down to 1 mm or less, is possible for the module inclusive of a rechargeable lithium polymer battery. The electronics module can be easily removed for garment maintenance (laundering).

19 Claims, 9 Drawing Sheets

(51) Int. Cl.
*G06F 1/16* (2006.01)
*A41D 1/00* (2006.01)
*H05K 3/00* (2006.01)

(52) U.S. Cl.
CPC . *H05K 3/0058* (2013.01); *H05K 2201/10037* (2013.01); *H05K 2201/10151* (2013.01); *Y10T 29/49* (2015.01); *Y10T 29/49018* (2015.01)

(56) References Cited

U.S. PATENT DOCUMENTS

| | | | |
|---|---|---|---|
| 5,572,401 | A | 11/1996 | Carroll |
| 5,669,393 | A | 9/1997 | Faisandier |
| 5,749,365 | A | 5/1998 | Magill |
| 6,047,203 | A | 4/2000 | Sackner et al. |
| 6,424,315 | B1 | 7/2002 | Glenn et al. |
| 6,454,708 | B1 | 9/2002 | Ferguson et al. |
| 6,471,087 | B1 | 10/2002 | Shusterman |
| 6,693,513 | B2 | 2/2004 | Tuttle |
| 6,774,865 | B1 | 8/2004 | Serra |
| 7,412,281 | B2 | 8/2008 | Shen et al. |
| 7,958,622 | B1 | 6/2011 | Ayala et al. |
| 8,099,794 | B2 | 1/2012 | Carstens |
| 2002/0084901 | A1* | 7/2002 | Mantyjarvi ............ A41D 1/005 340/573.1 |
| 2003/0127126 | A1 | 7/2003 | Yang |
| 2003/0224223 | A1 | 12/2003 | Edwards |
| 2005/0054941 | A1 | 3/2005 | Ting et al. |
| 2005/0285744 | A1 | 12/2005 | Tuttle |
| 2006/0211937 | A1 | 9/2006 | Eldridge |
| 2007/0038057 | A1 | 2/2007 | Nam et al. |
| 2007/0073131 | A1 | 3/2007 | Ryu et al. |
| 2007/0178716 | A1 | 8/2007 | Glaser et al. |
| 2007/0290862 | A1 | 12/2007 | Tuttle |
| 2007/0299325 | A1* | 12/2007 | Farrell ................. A61B 5/0002 600/301 |
| 2008/0009095 | A1 | 1/2008 | Charles, Jr. et al. |
| 2008/0125288 | A1* | 5/2008 | Case ....................... G06F 17/40 482/1 |
| 2009/0054737 | A1 | 2/2009 | Magar et al. |
| 2009/0261778 | A1 | 10/2009 | Kook |
| 2009/0306485 | A1 | 12/2009 | Bell |

OTHER PUBLICATIONS

Axisa, F, et al; "Flexible Technologies and Smart Clothing for Citizen Medicine, Home Healthcare, and Disease Prevention"; IEEE Transactions on Information Technology in Biomedicine, vol. 9, No. 3, Sep. 2005; p. 325-336.

Smith, T. "Smart Cards: Integrating for Portable Complexity"; Computer, Hewlett-Packard, Aug. 1998, p. 110-115.

Warren, S. "Wearable Telemonitoring Systems Designed with Interoperability in Mind"; Proceedings of the 25' Annual International Conference of the IEEE EMBS Cancun, Mexico Sep. 17-21, 2003; p. 3736-3739.

* cited by examiner

GARMENT FOR MONITORING PHYSIOLOGICAL FUNCTIONS AND METHOD OF USE THEREOF

CROSS-REFERENCE TO RELATED APPLICATIONS

This application is a divisional application of, prior-filed U.S. Nonprovisional application Ser. No. 12/503,600, filed on Jul. 15, 2009, which claims priority to and the benefit of prior-filed U.S. Provisional Application Ser. No. 61/080,704, filed on Jul. 15, 2008, the contents of each of which are herein incorporated by reference in their entireties.

BACKGROUND OF THE INVENTION

1. Field of the Invention

The present invention relates generally to physiological function monitors and, more particularly, to a garment utilizing a small, lightweight module for use in conjunction with sensors embedded in clothing.

2. Description of the Related Art

The need for real-time continuous monitoring of human physiological functions is becoming increasingly important due to the rapidly increasing over 60 population and the desire of baby boomers to monitor their vital signs and stay fit and the general trend in younger generations for fitness training. Also both amateur and professional athletes are pushing their bodies to the limit so real-time monitoring of their health status is of paramount importance.

Real-time monitoring or recording for later reading of physiological function data especially of exercisers and athletes has to be done in a non-intrusive, non-motion inhibiting manner yet it must provide reliable sensing and signal processing to transmit or store relevant information for the individual, coach and/or the physician. Key to this monitoring is the development of electronics matched to an appropriate sensing system.

Clothing containing sensors to monitor bodily physiological functions is not new, however, the major problem to date with electronically active or smart clothing is that the monitoring control and powering electronics always require a relatively large box (electronics plus battery) attached to the clothing or, in some cases, attached to a wrist band or a belt. Wires typically run from the garment containing the sensors to these boxes. Other embodiments have actually embedded these boxes into the garment thus causing difficulties in laundering. In some cases the sensors have to be attached directly to the body, using adhesives or conducting gels, such as is the case with wearable heart monitors.

In light of the above, there is a need for a wearable garment having electronics and sensors that can be configured to provide reliable data while being unintrusive and non-motion inhibiting to the wearer especially during exercising and can be safe during or easily removed for garment cleaning cycles.

SUMMARY OF THE INVENTION

Therefore, the present invention has been made in view of the above problems, and it is an objective of the present invention to eliminate or circumvent many, if not all, of the issues or limitations described above by providing a garment that can measure physiological functions especially during exercise without inhibiting the exerciser and yet is easy to launder after use.

In Applicants' invention a plurality of sensors are held in direct contact or close proximity to the person's body by being embedded in a form fitting garment similar to exercise togs. The sensors are connected via a plurality of embedded wires to an electronics module which is truly unintrusive being in one embodiment substantially the size of a credit card which is inclusive of the rechargeable lithium polymer battery. The electronics module can be easily removed for garment maintenance (laundering).

Therefore, the invention includes an electronics module connected to a plurality of sensors via a plurality of wires for use in a garment to monitor physiological functions, the electronics module comprising: a thin polymer battery; a first thin, multilayer substrate placed on and electrically connected to the battery; and a plurality of thinned integrated circuits placed on the first substrate.

The invention further includes a garment for monitoring a plurality of physiological functions comprising: a plurality of sensors for measuring the plurality of physiological functions, the sensors being embedded in the garment; an electronics module, the electronics module being substantially the size of a credit card, held in a pocket formed in the garment, and detachably connected to the plurality of sensors by a plurality of wires, the plurality of wires being woven into the garment; wherein the garment is form fitting in order to hold the plurality of sensors in contact with or close proximity to the body of a person exercising; and wherein the garment is washable upon the electronics module being detached from the plurality of wires and removed from the garment.

The invention further includes a method for monitoring physiological functions comprising: embedding a plurality of sensors in a garment; connecting a plurality of wires to the plurality of sensors; and connecting an electronics module to the plurality of wires, the electronics module comprising: placing a first thin, multilayer substrate on and electrically connecting it to a thin polymer battery; and placing a plurality of thinned integrated circuits on the first substrate.

The invention further includes a method for monitoring a plurality of physiological functions comprising: embedding a plurality of sensors for measuring the plurality of physiological functions in a garment, the garment being form fitting in order to hold the plurality of sensors in contact with or in close proximity to the body of the person exercising; connecting a plurality of wires to the plurality of sensors, the plurality of wires being woven into the garment; detachably connecting an electronics module to the plurality of wires, the electronics module being substantially the size of a credit card and held in a pocket formed in the garment; wherein the garment is washable upon the electronics module being detached from the plurality of wires and removed from the garment.

BRIEF DESCRIPTION OF THE DRAWINGS

These and other objects, features and advantages of the invention will be apparent from a consideration of the following Detailed Description considered in conjunction with the drawing Figures, in which.

DETAILED DESCRIPTION

In the following discussion, numerous specific details are set forth to provide a thorough understanding of the present invention. However, those skilled in the art will appreciate that the present invention may be practiced without such specific details. In other instances, well-known elements have been illustrated in schematic or block diagram form in order not to obscure the present invention in unnecessary detail.

The thinned die or integrated circuits discussed below are detailed more fully in U.S. patent application Ser. No. 11/756,816, filed Jun. 1, 2007, which is incorporated herein by reference in its entirety.

It should be noted that while the electronics module and garment of Applicants' invention were developed with exercisers and athletes in mind, the term "exercise" is broadly defined to include any bodily activity that enhances or maintains physical fitness and overall health. Furthermore, Applicants' invention is not to be limited to "exercise" as the invention may also be useful for physiological function monitoring in general.

Figure 1:
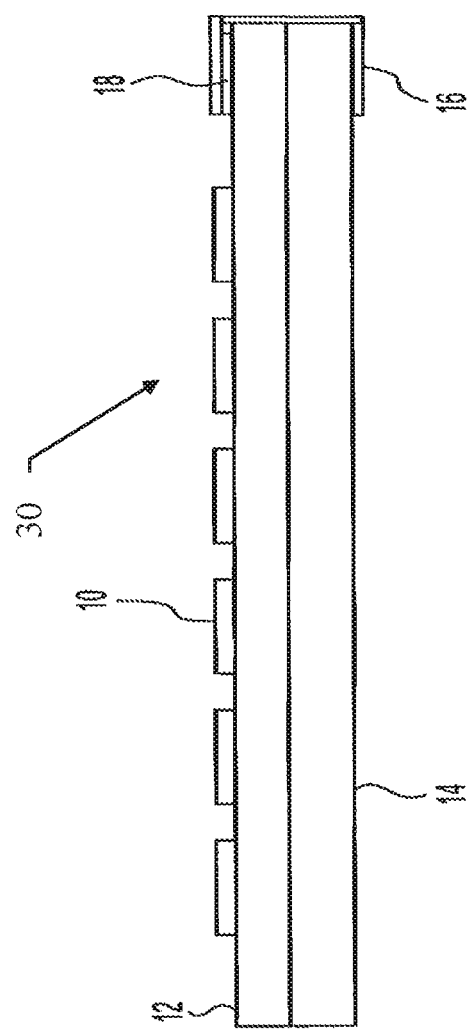
FIG. 1 illustrates a cross-section of the module of the invention.
Figure 2:
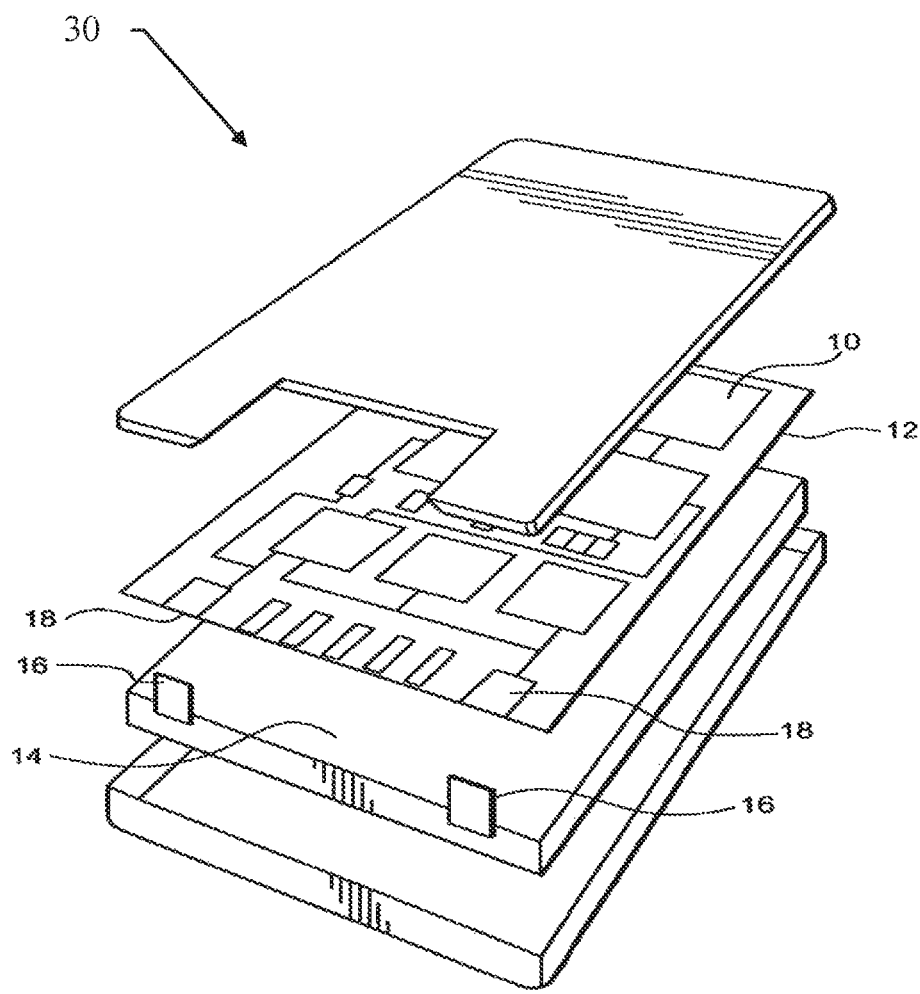
FIG. 2 illustrates an exploded view of the electronics module of the invention.
Figure 3:
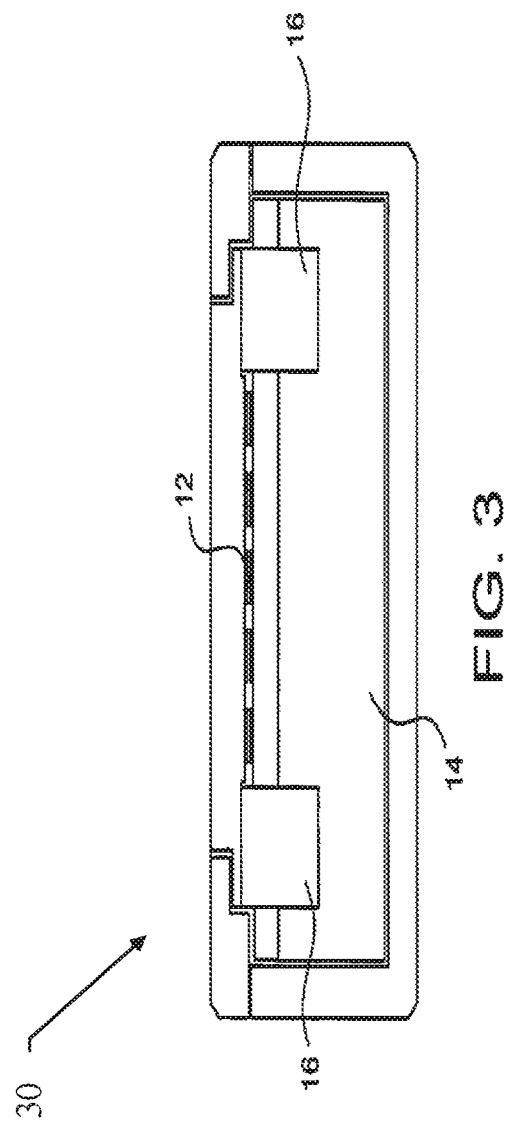
FIG. 3 illustrates an end view of the electronics module of the invention in a case.

FIGS. 1, 2, and 3 illustrate one embodiment of the invention. As noted above, in one embodiment, the electronics module 30 is substantially the size of a credit card, that is, 55 mm W×85 mm L×1 mm H. A range of thickness, from 6 mm (6 credit cards) down to 1 mm or less, is possible for the module 30 depending upon cost targets, the style of electronics (conventional or thinned); frequency and range of transmission; number of functions monitored; module display, if used; and, of course, comfort and ease of use by the wearer. These dimensions are inclusive of a rechargeable lithium polymer battery. While the electronics module 30 is discussed as being in the shape of a credit card, any shape may be possible depending on what is desired and how the electronics module 30 is manufactured.

In addition to its small size, the electronics module 30 is extremely light weight, weighing less than 25 grams (<1 oz) battery included. In the ultimate thin form, the weight will drop below 10 grams.

The module 30 will be highly functional and will have the capability of telemetering a range of physiological function data over a wireless link. The envisioned functionality (sensed physiological functions) and the power budget for each option is given in Table 1.

TABLE 1

Sensor Performance and Analysis

| Sensor | Power (mA @ 3 V) | # of Sensors | Sample Time per Sensor (sec) | Sampling Rate (Hz) | Total Power (mAH @ 3 V) | Modified Weight (gm) |
|---|---|---|---|---|---|---|
| Temperature | 0.14 | 20 | 0.15 | 0.02 | 0.0302 | 10 |
| Humidity | 1 | 20 | 0.15 | 0.02 | 0.2160 | 12 |
| Strain Gauges - Respiration | 0.14 | 2 | 0.15 | 1 | 0.1512 | 1 |
| Acoustics | 0.5 | 8 | 0.15 | 1 | 2.1600 | 10 |
| Pulse - Oximeter | 33.85 | 1 | 10 | 1 | 0.0094 | 21 |
| Galvanometer | 5 | 1 | 1 | 1 | 0.0014 | 5 |
| SHIRT SENSOR SUITE | | | | | 2.5682 | 59 |
| Sphygmomanometer | 3 | 1 | 60 | 0.1 | 0.0001 | 185 |
| Strain Gauges - Movement | 0.14 | 8 | 0.15 | 100 | 60.48 | 10 |
| OPTIONAL SENSORS | | 3 | | | 60.4801 | 195 |
| A/D | 0.5 | 4 | 121 | 1200 | 0.6667 | 1 |
| Microcontroller | 0.000022 | 1 | 60 | 60 | 0.0000 | 1 |
| Accelerometer | 0.18 | 1 | 1 | 60 | 0.0030 | 1 |
| Memory | 15 | 1 | 1 | 60 | 0.2500 | 1 |
| Battery (200 mAH) | | | | | | 10 |
| ELECTRONICS | | | | | 0.9197 | 14 |
| Total (W/O Optional Sensors) | | | | | 3.4879 | 73 |

Table 1 illustrates that with thin rechargeable lithium polymer batteries producing 50 to 200 mAH (which is currently within the capacity of commercially available thin lithium polymer batteries) the unit can be operative for 12 hours to 50 hours before a recharge would be necessary. This is more than enough time to accommodate a daily exercise routine, a twelve hour bike ride or hiking adventure or even 24 hour to several day heart monitoring activity (using pulse oximetry). In fact, the unit could provide monitoring for several days depending upon the size (thickness) of the polymer battery, the functionality selected and the frequency of transmission events.

For example, using thinned electronics coupled with a thicker polymer battery a 2 credit card thick module (that is, about 2 mm) could last up to two weeks (before a recharge is necessary) depending on how frequently the person monitors and transmits data. The electronics module 30 of the invention is envisioned to have full selectable or deselectable sensors and significant on board storage to simplify data transmission requirements.

Figure 4:
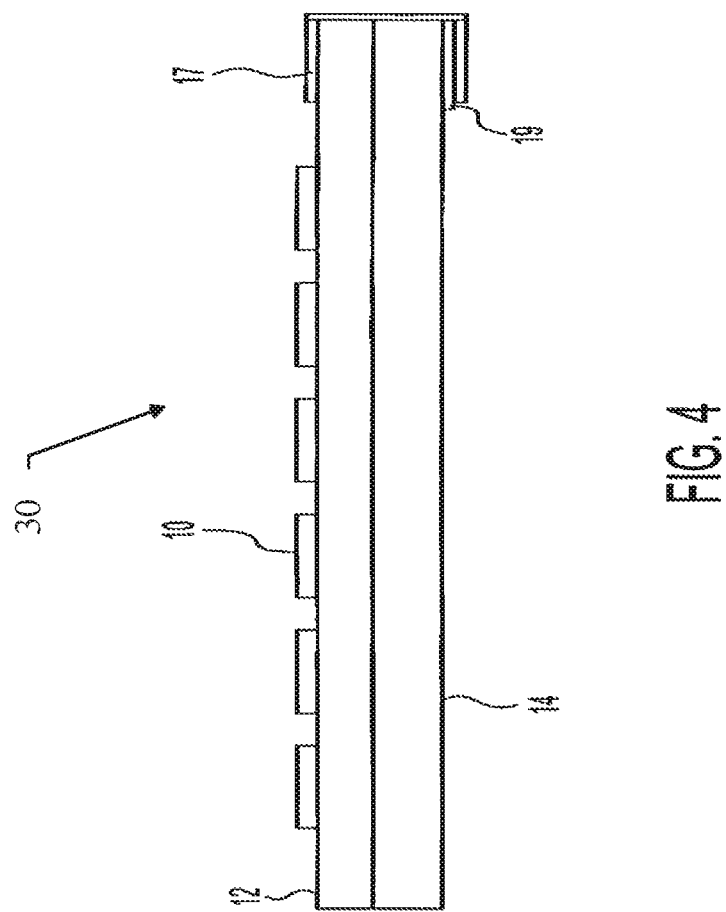
FIG. 4 illustrates a side view of one embodiment of the electronics module of the invention.

As shown in FIG. 1, the electronics module 30 of the invention comprises a thinned die or a plurality of integrated circuits (IC's) 10 with a first double-sided or ultra-thin multilayer (UTML) substrate 12 and a thin polymer battery 14. In one embodiment, shown in FIG. 1, extended flat leads 16 on the battery are wrapped around the UTML substrate to contact surface pads 18 on the UTML substrate. An exploded view of the module 30 in a hardshell case is shown in FIG. 2 and an unexploded cross-section view of the module 30 of FIG. 2 is shown in FIG. 3. In another embodiment shown in FIG. 4, the UTML substrate has leads 17 can be wrapped around the battery to contact the battery contacts/terminals 19. The entire module 30 can be laminated, hardshell encapsulated, or coated with a conformal polymer.

Figure 5:
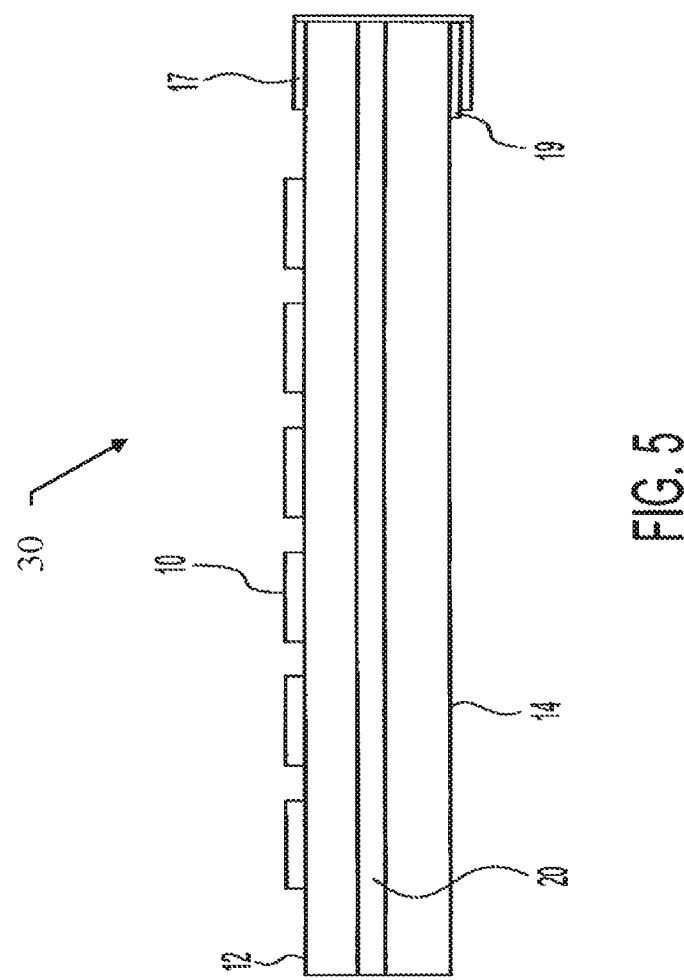
FIG. 5 illustrates a side view of another embodiment of the electronics module of the invention.
Figure 6:
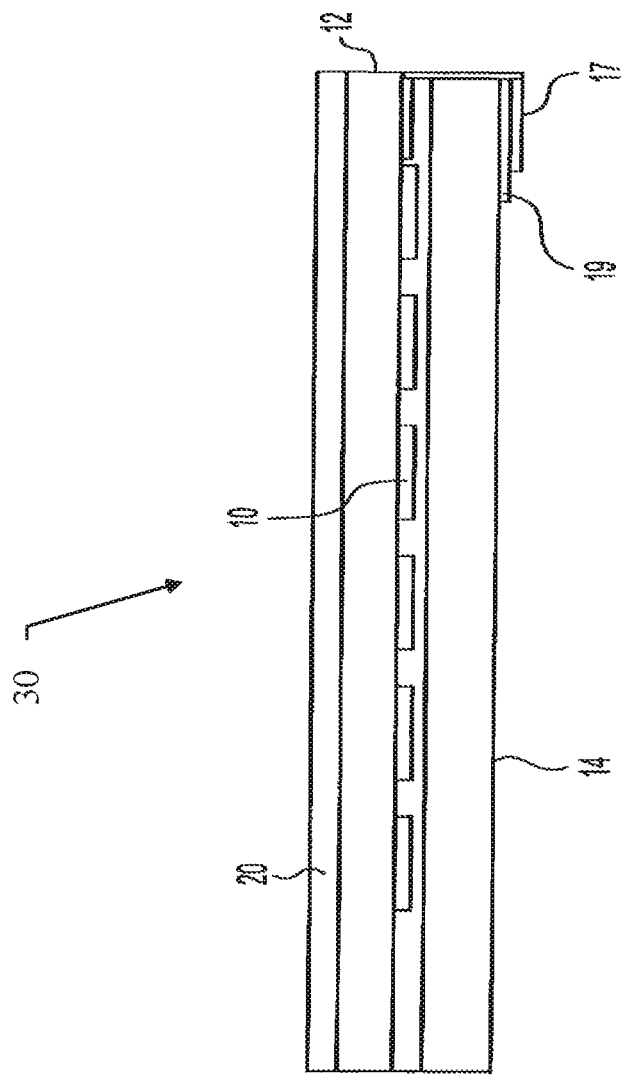
FIG. 6 illustrates a side view of another embodiment of the electronics module of the invention.

As shown in FIG. 5, a metallization layer 20 (typically the bottom layer) of the UTML can be patterned to form an integral antenna (not shown) necessary for wireless communication. This antenna can be placed next to the polymer battery for short range communication or the UTML can be inverted placing the antennas on the top of the module 30 for longer range transmission as shown in FIG. 6. In the standard configuration one of the polymer battery full plane electrode layers could serve as a ground plane for the antenna, if necessary. In addition to antennas, the UTML could have resistive and capacitive layers built in thus saving the precious surface area for active devices.

Figure 7:
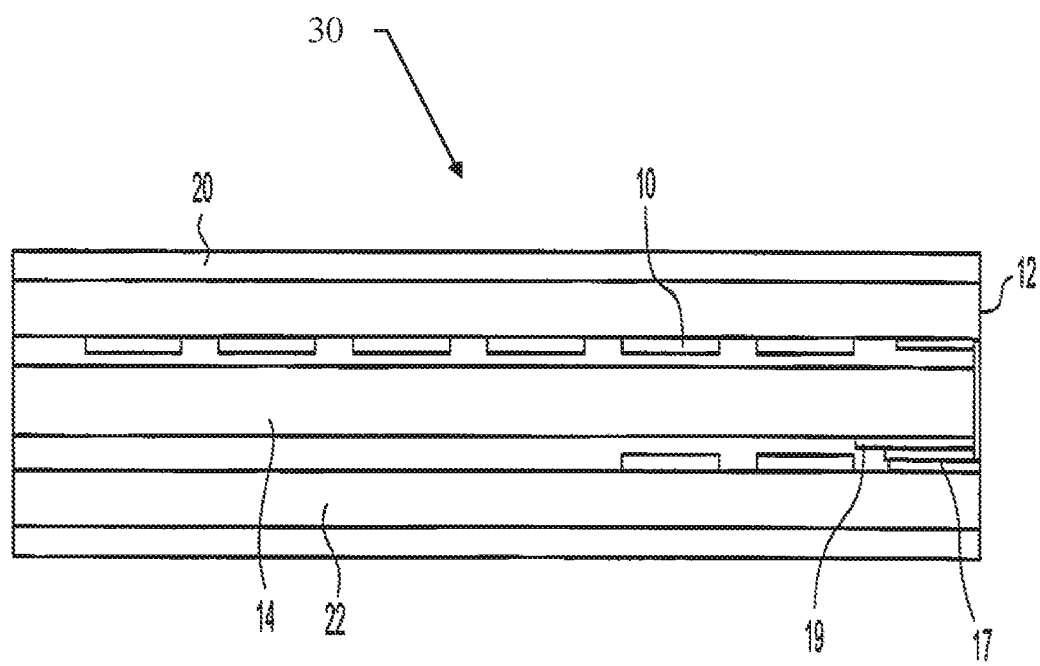
FIG. 7 illustrates a side view of another embodiment of the electronics module of the invention.

In another embodiment shown in FIG. 7, two UTMLs, the first 12 and a second 22 multilayer substrate, can be used in the module 30, the first containing the thinned die and sensor monitoring circuitry and the second placed on the bottom of the module 30 with the antennas and/or a first inductive loop or coil (not shown) for battery recharging without actual terminal contact. Recharging and perhaps reprogramming of the electronics could be done inductively.

A similar inductive link could be used to power up and communicate with the garment sensors. In this case, a third multilayer substrate (not shown) containing a second inductive coil (not shown) would be sewn into the garment. The matching first inductive coil would be on the surface of the electronics module 30. When placed in proximity both power and sensor signals can be transferred across the air interface.

Both milli-watts of power and digital signals in the several kilobits per second range can easily be transferred by inductive coils smaller than the credit card outline of the electronics module 30. With the close proximity, small misalignments will have little effect on power and signal transfer. The first and second inductive coils, the electronics module 30 and garment coils, respectively, can be protected by thin organic layers such as polyimide, acrylic, parylene, and silicon-based resins, thus the second inductive coil will suffer no degradation due to laundering. Similarly, since the electronics module 30 would have no exposed terminals, it would be more suitable for high moisture environments (e.g. perspiration, locker rooms, etc).

Figure 8:
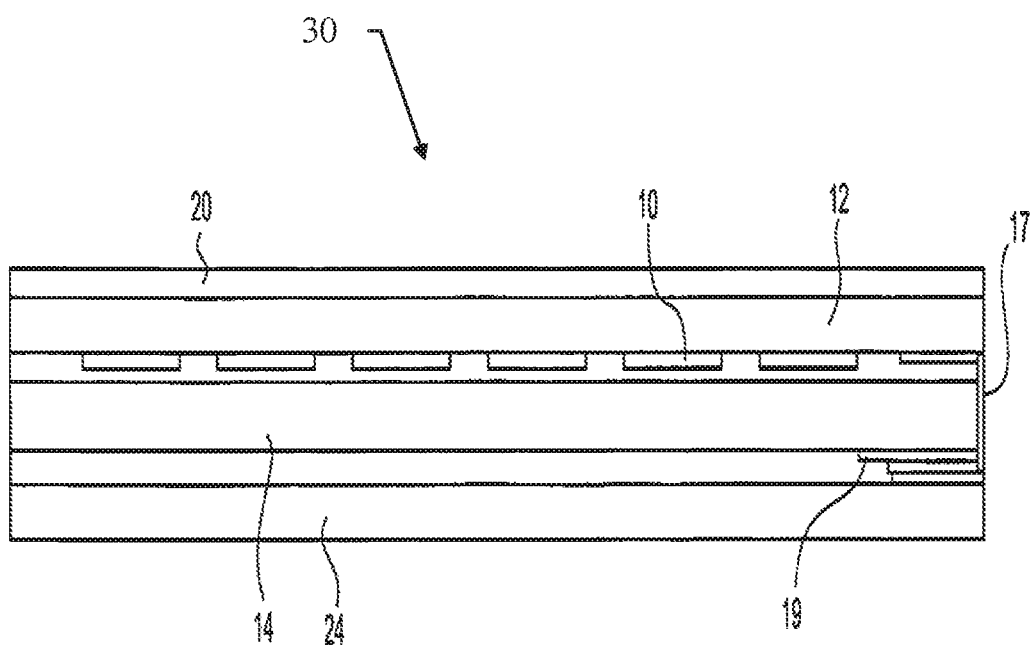
FIG. 8 illustrates a side view of another embodiment of the electronics module of the invention.

Given that silicon can be thinned using techniques referenced above, it is possible to use a thinned solar cell on the back of the module 30 as shown in FIG. 8. An integral solar cell 24 would recharge the battery if exposed to sunlight or even bright ambient light, thus a light transparent pocket in the garment would be necessary. This is easily accomplished for example on the back of cyclist's shirt, or the whole thin flexible system could be laminated to sports helmets. Thinning will reduce the efficiency of the solar cell, but with today's high performance cells, the resulting thinned cells should still have single digit efficiencies more than ample to recharge the electronics module 30 given a credit card sized area.

Figure 9:
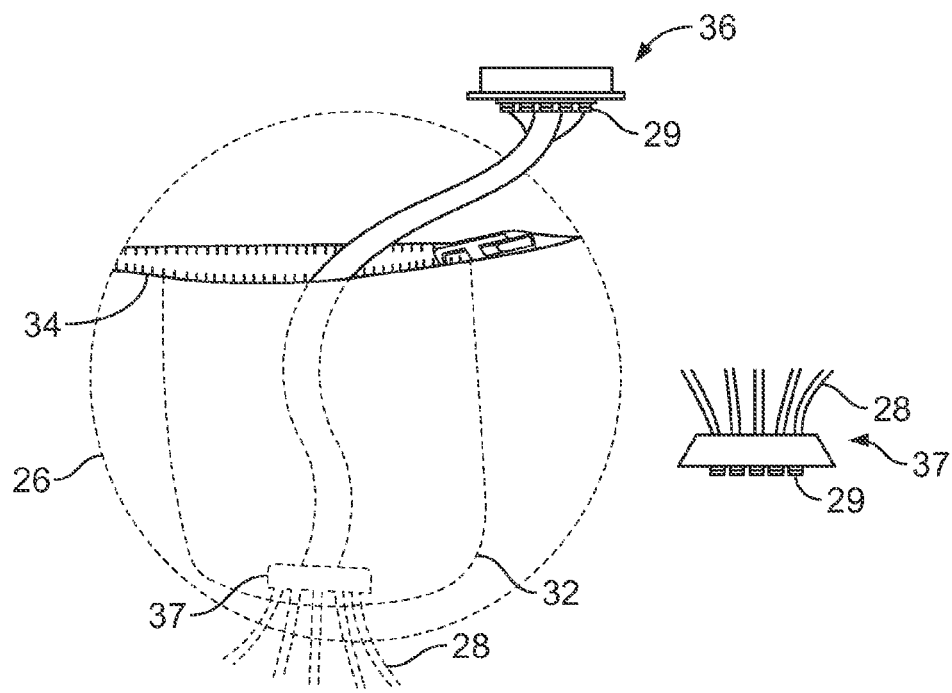
FIG. 9 illustrates both a "T" connector and a wedge connector for connecting the electronics module of the invention to the wires which connect the module to the sensors.
Figure 10:
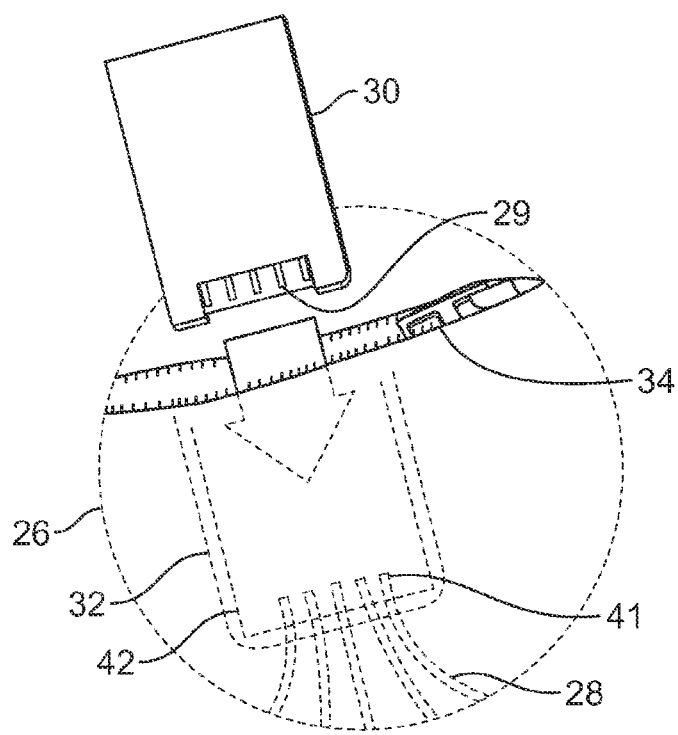
FIG. 10 illustrates a permanent "in pocket" reinforced backing connector for the electronics module of the invention.

A key element in the invention besides its obvious advantages of size, weight, and functionality is its easy attachment and removal from a garment 26 containing a plurality of sensors embedded therein, the sensors being connected to the electronics module 30 via a plurality of wires 28 and electrodes 29. Two examples of the module 30 to garment attachment mechanism are illustrated in FIGS. 9 and 10, but others are possible depending upon garment type, material, and the location of the electronics module attachment point. For most applications it is envisioned that the credit card thin module 30 (FIGS. 1-8) will be placed in a pocket 32 within the garment 26. The pocket 32 will be closed by, for example, a zipper 34 or, in another embodiment, VELCRO® (not shown).

One example of the sensor to electronics module attachment is shown in FIG. 9. This method uses a special "T" profile connector 36 which slips into a mating slot on the electronics module edge. The "T" connector 36 is attached to the plurality of sensors by a wedge connector 37 and the plurality of wires 28. Sufficient wire slack is allowed so that the "T" connector 36 and module 30 can be connected easily outside of the pocket 32 and then the wire and module 30 are placed in the pocket 32 and the pocket 32 is closed—thus protecting the module 30 during exercise, etc. The "T" connector 36 is keyed for correct insertion in the module 30 and together the module 30 and attached sensor connections would fit snuggly into the garment pocket 32 as mentioned above.

As shown in FIG. 10, an alternate connection scheme comprises a reinforced backing panel 40 placed in the garment pocket 32. This reinforced backing panel 40 would have sensor contacts 41 built in and contain guides 42 to ensure that when the electronics module 30 is inserted into the pocket 32 it makes tight contact with the sensor contacts 41. In this method the user would simply insert the electronics module 30 into the pocket guides 42, push the module 30 into position (seat the module 30) and then close the pocket 32. Thus, this method eliminates the need for the user to connect wires 28. The module guides 42 are keyed so that the module 30 can only be inserted in the correct direction. In its ultimate configuration, instead of connectors or module guides, optical transmission could be used to interrogate the sensors through embedded fiber optics.

Depending upon the selected mode of readout (wireless or contact) the station for reading and analyzing the data can vary. It can be a base station type where the 30 could also have an input device (touchpad/keyboard) to permit reprogramming of the module 30 functions (e.g. change the sampling rate, etc.). In this docking or base station configuration electrodes also engage the battery terminals to recharge the battery at the same time.

If the read out is accomplished remotely via wireless, then the read out and programming would be done on a computer located in the user's home, a doctor's office, or perhaps on the sidelines at a sporting event depending upon the operational scenario. Circuitry has been provided that will uniquely identify and/or serialize each module 30, thus, enabling a central monitoring station to identify which module 30 is sending the signal.

The electronic modules 30 could be customized for specialized applications such as home or hospital health monitoring, diagnosis, sports and fitness, etc. For example, a simplified version of the electronics module 30 (especially with an integral recharging system (solar cell)) could be mounted on baseball and football helmets to monitor impact strength, head motion, etc. Sensors would include strain gauges and accelerometers. This would be a safety (perhaps a flashing LED) system and would give a quick indication that both the forces received and reactive movements of the head exceeded preset threshold values.

While the invention has been described with reference to example embodiments, it will be understood by those skilled in the art that a variety of modifications, additions and deletions are within the scope of the invention, as defined by the following claims.

What is claimed is:

1. A garment for monitoring a plurality of physiological functions, said garment comprising:
   a plurality of sensors for measuring the plurality of physiological functions, the plurality of sensors being embedded in the garment; and
   an electronics module,
   wherein the electronics module is substantially the size of a credit card
   in order to be held in a pocket formed in the garment,
   wherein the electronics module is detachably connected to the plurality of sensors by a plurality of wires, the plurality of wires being woven into the garment,
   wherein the electronics module is configured to select or deselect one of the plurality of sensors,
   wherein the garment is form fitting in order to hold the plurality of sensors in contact with or close proximity to a body of a person exercising,
   wherein the garment is washable upon the electronics module being detached from the plurality of wires and removed from the garment, and
   wherein the electronics module comprises:
   a thin polymer battery;
   a first thin, multilayer substrate placed on and electrically connected to the battery;
   a plurality of thinned integrated circuits placed on the first thin, multilayer substrate;
   a second thin, multilayer substrate placed on an opposite side of the battery from the first thin, multilayer substrate, the second thin, multilayer substrate including an antenna patterned thereon and a first inductive coil patterned thereon for inductively recharging the battery and reprogramming the electronics module.

2. The garment as recited in claim 1, wherein the electronics module is configured to wirelessly transmit physiological data received from the plurality of sensors.

3. The garment as recited in claim 1, wherein the plurality of wires comprise fiber optics and physiological data received from the plurality of sensors is transmitted optically to the electronics module.

4. The garment as recited in claim 3, wherein after being detached from the plurality of wires, the electronics module is further configured to transmit the physiological data to a base station.

5. The garment as recited in claim 1,
   wherein the electronics module comprises an attachment mechanism for connecting the electronics module to the plurality of wires, and
   wherein the attachment mechanism is keyed to ensure a proper connection.

6. The garment as recited in claim 5, wherein the attachment mechanism is permanently installed in a pocket formed in the garment.

7. The garment as recited in claim 1, wherein a portion of the first thin, multilayer substrate is extended and wrapped around the battery to contact terminals of the battery.

8. The garment as recited in claim 7, wherein leads on the battery are extended and wrapped around the first thin, multilayer substrate to electrical contacts thereon.

9. The garment as recited in claim 1, the first thin, multilayer substrate including a plurality of resistive and capacitive layers formed therein to provide surface area for active devices contained in the plurality of thinned integrated circuits.

10. The garment as recited in claim 1, wherein the electronics module further comprises a third thin, multilayer substrate permanently connected to the plurality of wires and placed in the garment and having a second inductive coil patterned thereon, the second coil configured to inductively receive power from the first coil and transmit the physiological data from the plurality of sensors to the first inductive coil.

11. The garment as recited in claim 10, wherein the garment further comprises a protective layer placed on the first and second coils to protect against moisture.

12. The garment as recited in claim 11, wherein the protective layer comprises one of a thin organic and a silicon-based resin compound.

13. The garment as recited in claim 1, the electronics module further comprising a solar cell, the solar cell being thinned and disposed on the battery.

14. The garment as recited in claim 1, wherein the plurality of wires comprise fiber optics and physiological data received from the plurality of sensors is transmitted optically to the electronics module.

15. A method for monitoring a plurality of physiological functions, said method comprising:
    embedding a plurality of sensors for measuring the plurality of physiological functions in a garment, the garment being form fitting to hold the plurality of sensors in contact with or in close proximity to a body of a person exercising;
    connecting a plurality of wires to the plurality of sensors, the plurality of wires being woven into the garment;
    detachably connecting an electronics module to the plurality of wires, the electronics module being substantially the size of a credit card in order to be held in a pocket formed in the garment and comprising:
    a thin polymer battery;
    a first thin, multilayer substrate placed on and electrically connected to the battery;
    a plurality of thinned integrated circuits placed on the first thin, multilayer substrate;
    a second thin, multilayer substrate placed on an opposite side of the battery from the first thin, multilayer substrate, the second thin, multilayer substrate including an antenna patterned thereon and a first inductive coil patterned thereon for inductively recharging the battery and reprogramming the electronics module; and
    selecting or deselecting, via the electronics module, one of the plurality of sensors,
    wherein the garment is washable upon the electronics module being detached from the plurality of wires and removed from the garment.

16. The method as recited in claim 15, further comprising wirelessly transmitting, via the electronics module, physiological data received from the plurality of sensors.

17. The method as recited in claim 15, wherein
    detachably connecting the electronics module to the plurality of wires comprises detachably connecting the electronics module to the plurality of wires via an attachment mechanism, wherein the attachment mechanism is keyed to ensure a proper connection, and wherein the attachment mechanism is permanently installed in a pocket formed in the garment.

18. The method as recited in claim 15, wherein detachably connecting the electronics module to the plurality of wires further comprises detachably connecting the electronics module to the plurality of wires, the electronics module further comprising a solar cell, the solar cell being thinned and disposed on the battery.

19. The method as recited in claim 15, further comprising receiving physiological data from the plurality of sensors, and transmitting, via the plurality of wires, the physiological data to the electronics module.

* * * * *